United States Patent [19]
McIntyre

[11] Patent Number: 4,950,296
[45] Date of Patent: Aug. 21, 1990

[54] BONE GRAFTING UNITS

[76] Inventor: Jonathan L. McIntyre, 2384 Grove View Rd., San Diego, Calif. 92139

[21] Appl. No.: 365,766

[22] Filed: Jun. 13, 1989

Related U.S. Application Data

[63] Continuation-in-part of Ser. No. 179,282, Apr. 7, 1988, abandoned.

[51] Int. Cl.⁵ .............................................. A61F 2/28
[52] U.S. Cl. .......................................... 623/16; 606/76
[58] Field of Search ........................... 623/16, 66, 17; 128/92 R, 924 R, 924 G, 924 R, 924 S; 606/69, 70, 76, 86

[56] References Cited

U.S. PATENT DOCUMENTS 3,848,601 11/1974 Ma et al. ......................... 623/17 X
4,654,464 3/1987 Mittelmeier et al. ................ 623/16
4,678,470 7/1987 Nashef et al. ........................ 623/16
4,743,256 5/1988 Brantigan ......................... 623/16 X
4,834,757 5/1989 Brantigan ......................... 623/16 X

FOREIGN PATENT DOCUMENTS 3505567 6/1986 Fed. Rep. of Germany ........ 623/16
1309975 5/1987 U.S.S.R. .............................. 623/16

Primary Examiner—Alan Cannon
Attorney, Agent, or Firm—Baker, Maxham, Jester & Meador

[57] ABSTRACT

A bone grafting unit comprises a cortical shell having a selected outer shape and size for transplanting and a cavity formed therein for receiving a cancellous plug, and a cancellous plug fitted into said cavity in a manner to expose at least two surfaces thereof to the exterior of said shell.

15 Claims, 1 Drawing Sheet

U.S. Patent     Aug. 21, 1990     4,950,296
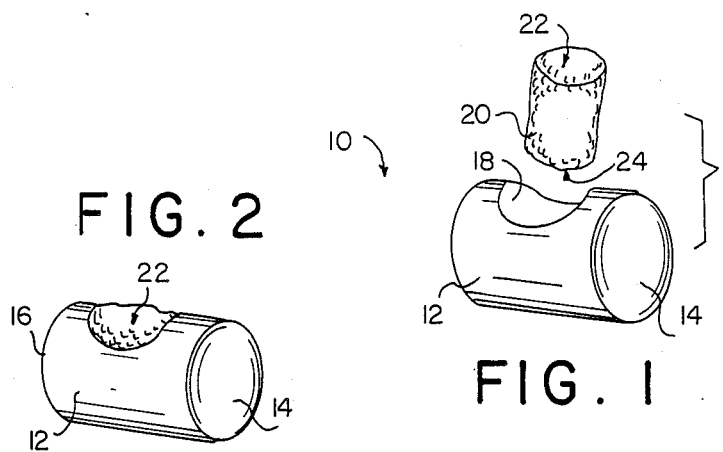
FIG. 2
FIG. 1
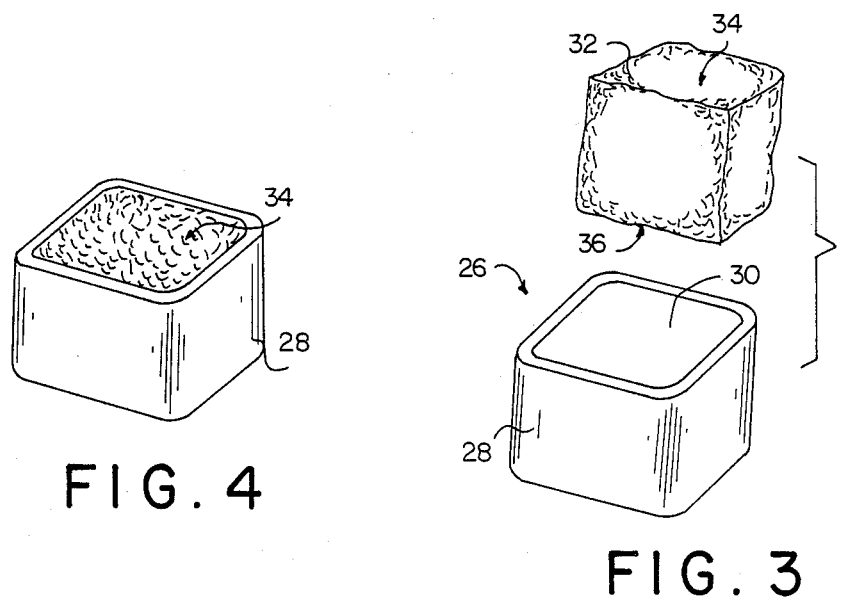
FIG. 4
FIG. 3

BONE GRAFTING UNITS

REFERENCE TO RELATED APPLICATION

The present application is a Continuation-in-Part of co-pending Application Ser. No. 07/179,282, filed Apr. 7, 1988, now abandoned, entitled "Integrated Cortical/Cancellous Device".

BACKGROUND OF THE INVENTION

The present invention relates to bone grafting units and pertains particularly to improved combined cortical cancellous bone graft units and methods of making same.

The repair of bone defects is a problem that has plagued orthopedics for many decades. In particular, the bridging of bone defects is one of the most challenging of these problems. Such defects may occur as the result of traumatic extrusion, radial tumor resection and massive sequestration as a result of infection. Bone transplant for repairing or correcting defects of this type is an approach that has been practiced for many years with a limited degree of success.

Many approaches to the provision of transplant plugs or units for repair of bone defects have been proposed in recent years. However, many of these have not been particularly satisfactory for most applications.

Fresh autogenous bone is considered the most desirable grafting material for several reasons, including lack of immune response. However, this approach requires secondary surgery which may be too severe and traumatic for the patient. There are also cases wherein sufficient quantities of autogenous bone are not available. The best site from which to obtain certain bone graft material is the left posterior ilium of the patient. However, neither this nor any other source from a living patient can supply certain requirements.

Allograft materials from bone banks and from cadavers is the most practical source of bone grafting materials for most requirements. While this source has a number of drawbacks also, most of them can be overcome by processing and preservation techniques.

One of the most desirable requirements of grafting material is that it be integrated into the adjacent bone or skeleton structure as quickly as possible. The spongy cancellous bone provides the most suitable matrix for rapid bone regeneration and repair. The relative loose structure of cancellous bone permits rapid and usually complete revascularization. This makes it most suitable for bone regeneration.

Another major requirement of most bone transplants is that it have strength and support capability. Cortical bone has high strength and is suitable for support structures. However, cortical bone revascularizes through preexisting periphery, but the process is rather slow and incomplete.

The applicant has devised a combination structure that provides both of these desirable qualities. This structure is a combined cortical cancellous bone graft unit.

SUMMARY AND OBJECTS OF THE INVENTION

It is the primary object of the present invention to provide an improved bone grafting unit and method of producing same.

In accordance with a primary aspect of the present invention, a bone grafting unit comprises the combination of a cortical shell having a cavity and an outer shape and size for transplanting, and a cancellous plug fitted into said cavity.

BRIEF DESCRIPTION OF THE DRAWING

The above and other objects and advantages of the present invention will become apparent from the following description when read in conjunction with the accompanying drawings wherein:

FIG. 1 is an exploded perspective view of a cortical cancellous dowel in accordance with the invention;

FIG. 2 is a perspective view of the assembled unit of FIG. 1;

FIG. 3 is an exploded perspective view of a cortical cancellous block (PLIF) in accordance with the invention; and FIG. 4 is a perspective view of the assembled unit of FIG. 4.

DETAILED DESCRIPTION OF A PREFERRED EMBODIMENT

Referring to FIG. 1, an integrated cortical cancellous dowel, in accordance with the invention and designated generally by the numeral 10, is illustrated. These dowels were devised and developed primarily for use as transplant plugs or units in the repair and/or treatment of ruptured lumbar intervertebral discs. They have also been developed for use in anterior cervical fusions. However, they may be used in other treatments.

The illustrated dowel comprises an elongated substantially cylindrical cortical body member 12, having a cylindrical outer surface with generally flat planar ends 14 and 16. A generally cylindrical cavity 18 is formed in and extending transverse to the axis of the body 12 for receiving a cancellous plug 20. The cavity is formed in the dowel so that the walls of the dowel body can be kept sufficiently thick to maintain adequate strength for structural support. In most cases, this means the walls should be at least 2 mm in thickness. For example, a #2 dowel has a 16 mm diameter. In order to maintain a 2 mm wall thickness, the cavity can be no more that 12 mm in diameter. In order to allow for a reasonable margin of error, a 10 mm cavity may be used.

A cancellous plug 20 is selected of the appropriate size to fit the cavity or bore 18. The plug is fitted to and mounted into the bore 18, preferably with a snug fit. The cavity or bore 18 preferably extends part way through the cortical body 12. However, it may extend completely through the body 12 to provide more exposure of the cancellous portion. This would present and expose opposite ends 22 and 24 of the cancellous plug 20 to both sides of the dowel body 12.

The dowel body 12 is taken from a suitable portion of the body where a sufficiently large cortical bone is available to provide the desired size dowel body. One suitable location is the cortical bone of the shaft of the femur. Other sources may be available for smaller dowel bodies if required. The dowel body 12 is preferably cut and formed by means of an appropriate size dowel cutter.

The cancellous plug 20 may be obtained from sources rich in cancellous material, such as the knee or the distal condyle. The resulting dowel or plug provides a device that has superior wall strength for support, and increased surface area that encourages tissue growth, vascularization, and deposition of new bone. As shown in FIG. 2, the large surface area 22 of cancellous bone is exposed to or at the outer surface of the dowel to provide optimum conditions for new tissue growth and fusion. The dowel may be used in any number of skeletal repair procedures, such as in fusion or securing adjacent bone surfaces together.

Referring to FIGS. 3 and 4, a generally cubically configured integrated cortical cancellous block 26 is illustrated. This block is formed and constructed in a manner similar to that of the dowel of FIG. 1. A suitable section of a femur or the like for the cortical shell is sectioned to provide an outer shell 28. The shell is cleaned and hollowed out to provide a cavity 30 for receiving a cancellous block 32. The shell 28 is selected and shaped to have a wall thickness of not less than 2 mm to provide the desired strength. The cavity 30 preferably extends entirely through the shell 28 and exposes large cancellous surfaces 34 and 36 of the block 32.

The cancellous block 32 is selected and sized to snugly fit the cavity 30 in the block 28, with top and bottom surfaces 34 and 36 exposed. This combination cortical and cancellous block provides a bridging segment, with the best features of both cortical and cancellous structures.

Grafting bone material may be obtained from any suitable source. A common source is that of cadavers wherein tissues are selected, cleaner, treated and preserved by well known techniques, such as by freezing, lyophilization and the like.

The transplant plugs or devices, in accordance with the invention as illustrated above, provides the surgeon with allograft bone that is consistent in size and quality, unlike those originating solely from the iliac crest. These devices also provide the surgeon with grafting blocks or units that have the combined and best characteristics of both cortical and cancellous bone materials. This combination of characteristics maximizes the chances of a successful transplant.

While I have illustrated and described my invention by means of specific embodiments, it is to be understood that numerous changes and modifications can be made therein without departing from the spirit and scope of the invention as defined in the appended claims.

I claim:

1. A bone grafting unit comprising in combination:
    a shell formed of cortical bone having cavity and an outer shape and size for transplanting into a position between opposed faces of a bone structure with said cavity open to one of said faces; and
    a plug formed of cancellous bone fitted into said cavity.

2. A bone grafting unit according to claim 1 wherein:
    said shell has a cylindrical configuration; and
    said cavity is transverse to the axis thereof.

3. A bone grafting unit according to claim 1 wherein:
    said cortical bone forming said shell is taken from the shaft of a femur.

4. A bone grafting unit according to claim 1 wherein:
    said cancellous bone forming said plug is taken from a knee.

5. A bone grafting unit according to claim 1 wherein:
    said cancellous plug is taken from the ilium of a subject.

6. A bone grafting unit according to claim 1 wherein:
    said shell is a section of a fermoral shaft.

7. A bone grafting unit according to claim 6 wherein:
    said cortical shell has an outer wall thickness of at least two mm.

8. A bone grafting unit according to claim 7 wherein:
    said cancellous plug is taken from a knee.

9. A bone grafting unit comprising in combination:
    a shell formed of a cortical bone having a selected outer shape and size for transplanting to a selected skeletal cite between opposed faces of a skeletal bone and a cavity formed therein for receiving a cancellous plug; and
    a cancellous plug formed of a cancellous bone fitted into said cavity in a manner to expose at least one surface thereof to the exterior of said shell.

10. A bone grafting unit according to claim 9 wherein:
    said shell has a cylindrical configuration; and
    said cavity is a cylindrical bore transverse to the axis thereof.

11. A bone grafting unit according to claim 10 wherein:
    said shell formed of a cortical bone is taken from the shaft of a femur.

12. A bone grafting unit according to claim 11 wherein:
    said cancellous bone forming said plug is taken from a knee.

13. A bone grafting unit according to claim 12 wherein:
    said cancellous bone forming said plug is taken from the ilium of a subject.

14. A bone grafting unit according to claim 10 wherein:
    said shell is a section of a fermoral shaft.

15. A bone grafting unit according to claim 14 wherein:
    said shell has an outer wall thickness of at least two mm.

* * * * *